(12) United States Patent
Klatt et al.

(10) Patent No.: US 9,995,813 B2
(45) Date of Patent: Jun. 12, 2018

(54) SAMPLE INTERVAL MODULATION MAGNETIC RESONANCE ELASTOGRAPHY

(71) Applicants: Dieter Klatt, Chicago, IL (US); Temel Kaya Yasar, Port Washington, NY (US)

(72) Inventors: Dieter Klatt, Chicago, IL (US); Temel Kaya Yasar, Port Washington, NY (US)

(73) Assignee: THE BOARD OF TRUSTEES OF THE UNIVERSITY OF ILLINOIS, Urbana, IL (US)

(*) Notice: Subject to any disclaimer, the term of this patent is extended or adjusted under 35 U.S.C. 154(b) by 460 days.

(21) Appl. No.: 14/648,081

(22) PCT Filed: Nov. 26, 2013

(86) PCT No.: PCT/US2013/071830
§ 371 (c)(1),
(2) Date: May 28, 2015

(87) PCT Pub. No.: WO2014/085376
PCT Pub. Date: Jun. 5, 2014

(65) Prior Publication Data
US 2015/0309145 A1  Oct. 29, 2015

Related U.S. Application Data

(60) Provisional application No. 61/732,009, filed on Nov. 30, 2012, provisional application No. 61/740,603, filed on Dec. 21, 2012.

(51) Int. Cl.
*G01V 3/00* (2006.01)
*G01R 33/563* (2006.01)
(Continued)

(52) U.S. Cl.
CPC ........ *G01R 33/56358* (2013.01); *A61B 5/055* (2013.01); *G01R 33/385* (2013.01)

(58) Field of Classification Search
CPC .............. G01R 33/34; G01R 33/34007; G01R 33/3635; G01R 33/48; G01R 33/4818;
(Continued)

(56) References Cited

U.S. PATENT DOCUMENTS

| 2010/0241012 A1* | 9/2010 | Yin | A61B 5/055 |
| | | | 600/485 |
| 2011/0006767 A1* | 1/2011 | Sack | A61B 5/055 |
| | | | 324/309 |

(Continued)

FOREIGN PATENT DOCUMENTS

WO   2012/145312   10/2012

OTHER PUBLICATIONS

Yeh WC, Li PC, Jeng YM, Hsu HC, Kuo PL, Li ML, Yang PM, Lee PH: Elastic modulus measurements of human liver and correlation with pathology. Ultrasound Med Biol 2002, 28(4):467-474.

(Continued)

*Primary Examiner* — Thang Le
(74) *Attorney, Agent, or Firm* — McDonnell Boehnen Hulbert & Berghoff LLP

(57) ABSTRACT

The invention disclosed herein provides methods for implementing Sampling Interval Modulation Magnetic Resonance Elastography ("SLIM-MRE"), based on simultaneous encoding and acquisition of individual displacement components using motion encoding gradients with different time discretization intervals to MRI analysis. The components are modulated with different frequencies in the MR signal phase, which can be expressed as a harmonic function of the start time, or equivalently of initial phase, of the motion encoding gradient components. As a result, all displacement components can be acquired faster than in conventional MRE, and can be derived from the same temporally-resolved MR phase images. This also allows for simultane- (Continued)

ously acquired 3D displacement data and storage of such data in the same k-space.

30 Claims, 8 Drawing Sheets

(51) Int. Cl.
*A61B 5/055* (2006.01)
*G01R 33/385* (2006.01)

(58) Field of Classification Search
CPC .............. G01R 33/481; G01R 33/4824; G01R 33/446; G01R 33/4835; G01R 33/4828; G01R 33/54; G01R 33/543; G01R 33/561; G01R 33/563; G01R 33/565; G01R 33/5611; G01R 33/5612; G01R 33/583; G01R 33/5659; G01R 33/56518; G01R 33/56536; G01R 33/56572; G01R 33/5614; G01R 33/5616; G01R 33/56509; G01R 33/341; G01R 33/385; G01R 33/56358; A61B 5/055; A61B 5/0555; A61B 5/7278; A61B 5/725
USPC .................................................. 324/300–322
See application file for complete search history.

(56) References Cited

U.S. PATENT DOCUMENTS

| | | | |
|---|---|---|---|
| 2011/0060210 A1* | 3/2011 | Ehman | A61B 5/055 600/410 |
| 2012/0130227 A1* | 5/2012 | McGee | A61B 5/055 600/411 |
| 2012/0274325 A1* | 11/2012 | Meaney | A61B 5/05 324/309 |
| 2013/0131490 A1* | 5/2013 | Huston, III | A61B 5/055 600/410 |
| 2014/0114177 A1* | 4/2014 | Chen | A61B 5/0051 600/415 |

OTHER PUBLICATIONS

Muthupillai R, Lomas DJ, Rossman PJ, Greenleaf JF, Manduca A, Ehman RL: Magnetic resonance elastography by direct visualization of propagating acoustic strain waves. Science 1995, 269(5232):1854-1857.
Asbach P, Klatt D, Schlosser B, Biermer M, Muche M, Rieger A, Loddenkemper C, Somasundaram R, Berg T, Hamm B et al: Viscoelasticity-based Staging of Hepatic Fibrosis with Multifrequency MR Elastography. Radiology 2010, 257(1):80-86.
Huwart L, Sempoux C, Salameh N, Jamart J, Annet L, Sinkus R, Peeters F, ter Beek LC, Horsmans Y, Van Beers BE: Liver fibrosis: noninvasive assessment with MR elastography versus aspartate aminotransferase-to-platelet ratio index. Radiology 2007, 245(2):458-466.
Yin M, Talwalkar JA, Glaser KJ, Manduca A, Grimm RC, Rossman PJ, Fidler JL, Ehman RL: A Preliminary Assessment of hepatic fibrosis with magnetic resonance elastography. Clin Gastroenterol Hepatol 2007, 5 (10):1207-1213.
Freimann FB, Streitberger KJ, Klatt D, Lin K, McLaughlin J, Braun J, Sprung C, Sack I: Alteration of brain viscoelasticity after shunt treatment in normal pressure hydrocephalus. Neuroradiology 2012, 54(3):189-196.
Murphy MC, Huston J, Jack CR, Glaser KJ, Manduca A, Felmlee JP, Ehman RL: Decreased Brain Stiffness in Alzheimer's Disease Determined by Magnetic Resonance Elastography. J Magn Reson Imaging 2011, 34(3):494-498.
Schregel K, Tysiak EWN, Garteiser P, Gemeinhardt I, Prozorovski T, Aktas O, Merz H, Petersen D, Wuerfel J, Sinkus R: Demyelination reduces brain parenchymal stiffness quantified in vivo by magnetic resonance elastography. Proceedings of the National Academy of Sciences of the United States of America 2012, 109(17):6650-6655.
Würfel J, Paul F, Beierbach B, Hamhaber U, Klatt D, Papazoglou S, Zipp F, Martus P, Braun J, Sack I: MR-elastography reveals degradation of tissue integrity in multiple sclerosis. NeuroImage 2010, 49(3):2520-2525.
Manduca A, Oliphant TE, Dresner MA, Mahowald JL, Kruse SA, Amromin E, Felmlee JP, Greenleaf JF, Ehman RL: Magnetic resonance elastography: Non-invasive mapping of tissue elasticity. Medical Image Analysis 2001, 5 (4):237-254.
Van Houten EEW, Viviers DV, McGarry MDJ, Perrinez PR, Perreard II, Weaver JB, Paulsen KD: Subzone based magnetic resonance elastography using a Rayleigh damped material model. Med Phys 2011, 38(4):1993-2004.
McGarry MDJ, Van Houten EEW, Johnson CL, Georgiadis JG, Sutton BP, Weaver JB, Paulsen KD: Multiresolution MR elastography using nonlinear inversion. Med Phys 2012, 39(10):6388-6396.
Papazoglou S, Hirsch S, Braun J, Sack I: Multifrequency inversion in magnetic resonance elastography. Physics in medicine and biology 2012, 57(8):2329-2346.
Lewa CJ, De Certaines JD: Viscoelastic property detection by elastic displacement NMR measurements. J Magn Reson Imaging 1996, 6(4):652-656.
Plewes DB, Betty I, Urchuk SN, Soutar I: Visualizing tissue compliance with MR imaging. J Magn Reson Imaging 1995, 5(6):733-738.
Klatt D, Asbach P, Rump J, Papazoglou S, Somasundaram R, Modrow J, Braun J, Sack I: In vivo determination of hepatic stiffness using steady-state free precession magnetic resonance elastography. Invest Radiol 2006, 41(12):841-848.
Clayton EH, Garbow JR, Bayly PV: Frequency-dependent viscoelastic parameters of mouse brain tissue estimated by MR elastography. Physics in medicine and biology 2011, 56(8):2391-2406.
Klatt D, Hamhaber U, Asbach P, Braun J, Sack I: Noninvasive assessment of the rheological behavior of human organs using multifrequency MR elastography: a study of brain and liver viscoelasticity. Physics in medicine and biology 2007, 52(24):7281-7294.
Sinkus R, Tanter M, Xydeas T, Catheline S, Bercoff J, Fink M: Viscoelastic shear properties of in vivo breast lesions measured by MR elastography. Magn Reson Imaging 2005, 23(2):159-165.
Johnson CL, McGarry MD, Gharibans AA, Weaver JB, Paulsen KD, Wang H, Olivero WC, Sutton BP, Georgiadis JG: Local mechanical properties of white matter structures in the human brain. NeuroImage 2013, 79:145-152.
Pattison AJ, Lollis SS, Perrinez PR, Perreard IM, McGarry MDJ, Weaver JB, Paulsen KD: Time-harmonic magnetic resonance elastography of the normal feline brain. J Biomech 2010, 43(14):2747-2752.
Qin EC, Sinkus R, Geng GQ, Cheng S, Green M, Rae CD, Bilston LE: Combining MR elastography and diffusion tensor imaging for the assessment of anisotropic mechanical properties: A phantom study. J Magn Reson Imaging 2013, 37(1):217-226.
Hirsch S, Klatt D, Freimann FB, Scheel M, Braun J, Sack I: In vivo measurement of volumetric strain in the human brain induced by arterial pulsation and harmonic waves. Magn Reson Med 2013, online ahead of print; DOI:10.1002/mrm.24499.
Romano A, Scheel M, Hirsch S, Braun J, Sack I: In vivo waveguide elastography of white matter tracts in the human brain. Magn Reson Med 2012, 68(5):1410-1422.
Yasar TK, Klatt D, Magin RL, Royston TJ: Selective spectral displacement projection for multifrequency MRE. Physics in medicine and biology 2013, 58(16):5771-5781.
Yin M, Woollard J, Wang X, Torres VE, Harris PC, Ward CJ, Glaser KJ, Manduca A, Ehman RL: Quantitative assessment of hepatic fibrosis in an animal model with magnetic resonance elastography. Magn Reson Med 2007, 58(2):346-353.
Yasar T, Royston TJ, Magin RL: Wideband MR elastography for viscoelasticity model identification. Magn Reson Med 2013, 70:479-489.

(56) References Cited

OTHER PUBLICATIONS

Zhang J, Green MA, Sinkus R, Bilston LE: Viscoelastic properties of human cerebellum using magnetic resonance elastography. J Biomech 2011, 44(10):909-1913.

Glaser KJ, Manduca A, Ehman RL: Review of MR elastography applications and recent developments. J Magn Reson Imaging 2012, 36(4):757-774.

Royston TJ, Yasar TK, Magin RL: Geometric Focusing of High Frequency Shear Waves for Noninvasive High Resolution MR Elastography. In: Proc 19th Annual Meeting ISMRM. Montreal; 2011: 3481.

Knutsson H, Westin CJ, Granlund G: Local multiscale frequency and bandwidth estimation. In: Proc of the IEEE Intl Conf on Image Processing: 1994; 1994: 36-40.

Bernstein MA, Zhou XHJ, Polzin JA, King KF, Ganin A, Pelc NJ, Glover GH: Concomitant gradient terms in phase contrast MR: Analysis and correction. Magn Reson Med 1998, 39(2):300-308.

Rump J, Klatt D, Braun J, Warmuth C, Sack I: Fractional Encoding of Harmonic Motions in MR Elastography. Magnetic Resonance in Medicine (2007) 57:388-395.

Sack I, Mcgowan CK, Samani A, Luginbuhl C, Oakden W, Plewes DB: Observation of Nonlinear Shear Wave Propagation Using Magnetic Resonance Elastography. Magnetic Resonance in Medicine 2004, 52:842-850.

Oliphant, T. E. et al.: "Comples-valued stiffness reconstruction for magnetic resonance elastography by algebraic inversion of the differential equation," Magentic Resonance in Medicine, Academic Press, Duluth, MN, US, vol. 45, No. 2, Feb. 1, 2001, pp. 299-310.

\* cited by examiner

| | $j=1$ | | | $j=2$ | | | $j=3$ | | |
|---|---|---|---|---|---|---|---|---|---|
| $n$ | $s_1$ (i) | $s_1$ (ii) | $s_1$ (iii) | $s_2$ (i) | $s_2$ (ii) | $s_2$ (iii) | $s_3$ (i) | $s_3$ (ii) | $s_3$ (iii) |
| 0 | 0 | 0 | 0 | 0 | 0 | 0 | 0 | 0 | 0 |
| 1 | $\frac{1}{8f}$ | $\frac{1}{8f}$ | 25 | $\frac{2}{8f}$ | $\frac{2}{8f}$ | 50 | $\frac{3}{8f}$ | $\frac{3}{8f}$ | 75 |
| 2 | $\frac{2}{8f}$ | $\frac{2}{8f}$ | 50 | $\frac{4}{8f}$ | $\frac{4}{8f}$ | 100 | $\frac{6}{8f}$ | $\frac{6}{8f}$ | 150 |
| 3 | $\frac{3}{8f}$ | $\frac{3}{8f}$ | 75 | $\frac{6}{8f}$ | $\frac{6}{8f}$ | 150 | $\frac{9}{8f}$ | $\frac{1}{8f}$ | 25 |
| 4 | $\frac{4}{8f}$ | $\frac{4}{8f}$ | 100 | $\frac{8}{8f}$ | 0 | 0 | $\frac{12}{8f}$ | $\frac{4}{8f}$ | 100 |
| 5 | $\frac{5}{8f}$ | $\frac{5}{8f}$ | 125 | $\frac{10}{8f}$ | $\frac{2}{8f}$ | 50 | $\frac{15}{8f}$ | $\frac{7}{8f}$ | 175 |
| 6 | $\frac{6}{8f}$ | $\frac{6}{8f}$ | 150 | $\frac{12}{8f}$ | $\frac{4}{8f}$ | 100 | $\frac{18}{8f}$ | $\frac{2}{8f}$ | 50 |
| 7 | $\frac{7}{8f}$ | $\frac{7}{8f}$ | 175 | $\frac{14}{8f}$ | $\frac{6}{8f}$ | 150 | $\frac{21}{8f}$ | $\frac{5}{8f}$ | 125 |

FIG. 8

SAMPLE INTERVAL MODULATION MAGNETIC RESONANCE ELASTOGRAPHY

This Application is a US national phase of International Application No. PCT/US2013/071830 filed on Nov. 26, 2013, which claims the benefit of priority to both of U.S. Provisional Application 61/732,009 filed Nov. 30, 2012 and U.S. Provisional Application 61/740,603 filed Dec. 21, 2012, all three of which are incorporated by reference herein in their entirety.

BACKGROUND

Magnetic resonance imaging (MRI) is commonly used to image the internal tissues of a subject. Magnetic resonance elastography (MRE) is a technique for determining mechanical properties of a subject under study by introducing mechanical vibrations in the subject undergoing MRI.

MRI is typically performed by placing the subject or object to be imaged at or near the isocenter of a strong, uniform magnetic field, $B_0$, known as the main magnetic field. The main magnetic field causes the atomic nuclei (spins) that possess a magnetic moment in the matter comprising the subject or object to become aligned in the magnetic field. The spins form a magnetization that precesses around the magnetic field direction at a rate proportional to the magnetic field strength. For hydrogen nuclei (which are the common nuclei employed in MRI), the precession frequency is approximately 64 MHz in a magnetic field of 1.5 Tesla. If the magnetization is perturbed by a small radio-frequency magnetic field, known as a $B_1$ magnetic field, the spins emit radiation at a characteristic radio frequency (RF). The emitted RF radiation can be detected and analyzed to yield information that may be used to produce an image of the subject or object. For purposes of the discussion herein, the term "object" will be used to refer to either a subject (e.g., a person) or an object (e.g., a test object) when describing magnetic resonance imaging of that "object."

In practice, magnetic field gradients are also applied to the subject or object in addition to the main magnetic field. The field gradients are typically applied along one or more orthogonal axes, (x, y, z), the z-axis usually being aligned with the $B_0$, and introduce spatially-distributed variations in frequency and/or phase of the precessing nuclear spins. By applying the radio-frequency $B_1$ magnetic field and gradient fields in carefully devised pulses and/or sequences of pulses that are switched on and off, the RF radiation emitted can carry spatially encoded information that, when detected and analyzed, can be used to produce detailed, high resolution images of the subject or object. Various techniques utilizing both specific pulse sequences and advanced image reconstruction methods have been developed, providing new advances, as well as introducing new challenges.

An MRI system typically includes hardware components, including a plurality of gradient coils positioned about a bore of a magnet, an RF transceiver system, and an RF switch controlled by a pulse module to transmit RF signals to and receive RF signals from an RF coil assembly. The received RF signals are also known as magnetic resonance (MR) signal data. An MRI system also typically includes a computer programmed to cause the system to apply to an object in the system various RF signals, magnetic fields, and field gradients for inducing spin excitations and spatial encoding in an object, to acquire MR signal data from the object, to process the MR signal data, and to construct an MR image of the object from the processed MR signal data. The computer can include one or more general or special purpose processors, one or more forms of memory, and one or more hardware and/or software interfaces for interacting with and/or controlling other hardware components of the MRI system.

MR signal data detected from an object are typically described in mathematical terms as "k-space" data (k-space is the Fourier inverse of image or actual space). An image in actual space is produced by a Fourier transform of the k-space data. MR signal data are acquired by traversing k-space over the course of applying to the object the various RF pulses and magnetic field gradients. In practice, techniques for acquiring MR signal data from an object are closely related to techniques for applying the various RF pulses and magnetic field gradients to the object.

In MRE, external vibrations are introduced into an object, such as biologic tissue, under examination. Vibrations in the tissue (or object) are encoded in the MR signal phase using standard MRI sequences upgraded with motion encoding gradients (MEG). As a result, tissue mechanical parameters can be calculated from the acquired wave fields. In the study of live subjects, the analysis of MRE data with one motion-encoding direction can reveal a correlation of pathophysiological changes and the mechanical behavior of diverse organs. However, difficulties in resolving early disease stages have also become apparent. A step towards a higher diagnostic accuracy is represented by the acquisition of the three-dimensional (3D) displacement field, by which it becomes possible to separate shear from a compression wave by using the curl-operator, and which sets asides any assumptions about the direction of wave propagation in the wave field inversion algorithm.

In MRE, measurement time may be of interest. Aside from cost factors, long acquisition times may have the potential of decreasing measurement accuracy, since motion may occur and cause misalignment of the images. Further, in conventional 3D MRE, the components of the tissue (or object) displacement are acquired in three individual temporally resolved MRE experiments carried out sequentially in time. Therefore, the components, although attributed to the same point in time, are actually acquired in different physiological states of the subject.

Accordingly, there is a need to improve the method for imaging and analyzing tissue samples using MRE techniques.

SUMMARY

This invention provides improved imaging and tissue sample analysis using MRE techniques having better time efficiency and robustness by imaging a tissue sample in all three dimensions, simultaneously, while retaining high-quality imaging resolution.

Example embodiments are disclosed herein for applying MEG in an arrangement capable of encoding three spatial components of a mono-frequency tissue vibration simultaneously. The method, referred to herein as "Sampling Interval Modulation Magnetic Resonance Elastography" (SLIM-MRE), employs different time discretization intervals in each of the individual displacement components. In doing so, the components are modulated with different frequencies in the MR signal phase. Simultaneous application of three spatial components of the MEG, while accounting for the SLIM-concept, enables all displacement components to be acquired faster than in conventional MRE, and allows the displacements in the different spatial dimensions to be derived from the same temporally-resolved MR phase images. The techniques also allow for simultaneously acquisition of 3D displacement data, as well as storage of such data in the same k-space.

Example embodiments SLIM-MRE disclosed herein provide a method and system to collect and analyze 3D displacement data that are simultaneously acquired and stored in the same k-space. This simultaneous application of MEG in three dimensions and the simultaneous acquisition in three dimensions of MRE data is superior to conventional methods used for the collection and analysis of MRE data because it both allows collection of tissue sample data points in three dimensions during the same time period, and simultaneously reduces the amount of time to collect and analyze such data, without diminishing the quality of data or analysis.

One aspect of example embodiments provided herein is a method for calculating a mechanical property of a tissue by using an MRI system. This method includes using the MRI system to acquire MRE data from a sample (or object), and reconstructing images for analysis based on the MRE data, and to do so by acquiring all three motion components of a mono-frequency vibration simultaneously and storing them in the same k-space.

In another aspect of example embodiments provided herein, each of the three spatial components are observed using a different time discretization interval.

In another aspect of the invention, the three spatial components of the mono-frequency vibration are stored in a same k-space.

In another aspect of example embodiments provided herein, no greater than eight samples are used for temporal resolution to decompose the three spatial components.

In yet another aspect of example embodiments provided herein, the three spatial components were encoded with different frequencies in an MR phase.

Hence, in one aspect, various embodiments of the present invention provide, in a magnetic resonance imaging (MRI) system, a computer-implemented method comprising: while inducing a mechanical vibration in an object in the MRI system, applying a magnetic resonance (MR) signal to the object, the MR signal having a phase; encoding vibrational motion of the object in the MR signal phase simultaneously in three spatial dimensions by applying a motion encoding gradient (MEG) to the object simultaneously in the three spatial dimensions; and simultaneously acquiring in all three of the spatial dimensions magnetic resonance elastography (MRE) data including the MR signal phase encoded with the vibrational motion of the object in the three spatial dimensions.

In another aspect, various embodiments of the present invention provide magnetic resonance imaging (MRI) system comprising: one or more processors; memory; a main magnet; one or more gradient coils; and machine-readable instructions stored in the memory that, when executed by the one or more processors, cause the MRI system to carry out functions including: inducing a mechanical vibration in an object in the MRI system, while applying a magnetic resonance (MR) signal to the object, wherein the MR signal has a phase; encoding vibrational motion of the object in the MR signal phase simultaneously in three spatial dimensions by applying a motion encoding gradient (MEG) to the object simultaneously in the three spatial dimensions; and simultaneously acquiring in all three of the spatial dimensions magnetic resonance elastography (MRE) data including the MR signal phase encoded with the vibrational motion of the object in the three spatial dimensions.

These as well as other aspects, advantages, and alternatives will become apparent to those of ordinary skill in the art by reading the following detailed description, with reference where appropriate to the accompanying drawings. Further, it should be understood that this summary and other descriptions and figures provided herein are intended to illustrate the invention by way of example only and, as such, that numerous variations are possible.

BRIEF DESCRIPTION OF THE DRAWINGS

FIG. 8 presents a table of MEG start times, in accordance with an example embodiment.

DETAILED DESCRIPTION

1. Overview

Derivation of an analytical formulation of SLIM-MRE can start from standard MRE equations. The basic equation of MRE in three spatial dimensions indexed by j=1, 2, 3, is represented by $$\phi = \gamma \Sigma_{j=1}^{3} \int_{s_j}^{s_j+T} G_j(t) \cdot u_j(t) dt, \quad (1)$$

which describes the encoding of the displacement $u_j$ of an isochromat in the MR signal phase $\phi$ by applying a magnetic field gradient $G_j$. In Equation (1), $\gamma$, T, and $s_j$ denote the gyromagnetic ratio of the proton, the duration of the application of the MEG, and the start time of the MEG component in the jth direction, respectively. As discussed below, the basic equation of MRE as expressed in Equation (1), which accounts for three spatial dimensions, can be adapted for application in SLIM-MRE. In particular, in SLIM-MRE, T may be kept constant for all MEG components, while $s_j$ may be varied under an assumption that the displacement can be represented by a harmonic vibration and that the MEG components are bipolar.

As described in more detail below, equation (1) can be solved in a form relating an initial mechanical phase $\Theta_j$, an amplitude $u_j^0$ and an encoding efficiency $\xi_j$ of the displacement component $u_j$. By doing so, MR signal phase may be expressed as:

$$\phi = \sum_{j=1}^{3} \varphi_j(s_j) = \sum_{j=1}^{3} \xi_j u_j^0 \sin(2\pi f s_j + \Theta_j + \frac{\pi}{2}). \quad (2)$$

Temporal resolution can be specified in terms of a variation of the MEG-start time. More particularly, in SLIM-MRE, a different MEG start time can be used for each of the three MEG components. The MEG start time in each dimension can take the form $s_{jn}=n\Delta t_j$, $n=0, 1, \ldots, N-1$, where N is the number of samples and $$\Delta t_j = \frac{j}{fN},$$

$j=1, 2, 3$ gives the sampling interval in the three dimensions. The solved MRE equation can thus be discretized such that the three displacement components are encoded with different "apparent frequencies" representing the first, second, and third harmonics. The discretized form of Equation (2) then becomes $$\phi_n = \sum_{j=1}^{3} \varphi_j(s_{jn}) = \sum_{j=1}^{3} \xi_j u_j^0 \sin\left(2\pi j \frac{n}{N} + \Theta_j + \frac{\pi}{2}\right). \quad (3)$$

The individual components can thus be decomposed by applying a discrete Fourier transform to $\phi_n$.

Figure 1:
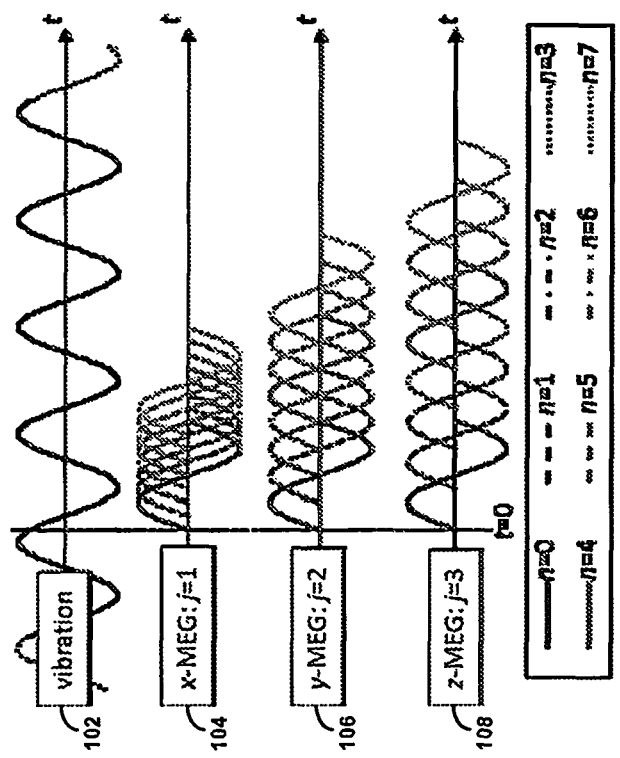
FIG. 1 illustrates simultaneous application of three spatial components of magnetic encoding gradients for an example of eight sampling intervals, in accordance with an example embodiment.

The variation in MEG start times for the different dimensions can be visualized with reference to FIG. 1, which illustrates an arrangement of applied MEGs relative to the mechanical actuation signal, in accordance with SLIM-MRE. A vibration 102 with a consistent amplitude and frequency f is represented as a sinusoidal function of time in the top panel of the Figure. An MEG component in each of three spatial dimensions is shown respectively in each of the three panels below the top panel. Specifically, x, y, and z components of the MEG are identified in FIG. 1 as x-MEG 104, y-MEG 106, and z-MEG 108, with the three spatial dimensions (and the corresponding MEG components) indexed by $j=1, 2, 3$, respectively. By way of example, each MEG component is represented as a sinusoidal function of time with the same frequency as the vibration 102. For purposes of brevity in the Figure, just one MEG cycle of each MEG sample interval for each of eight samples is shown in each dimension; as a visual cue, a different line style is used for each sample.

In the example illustrated in FIG. 1, the start time of each MEG of duration T in each dimension is measured with respect to time $t=0$. In each dimension j, the MEG start time of each successive sample increases by $\Delta t_j$, corresponding to a sampling frequency given by the inverse of $\Delta t_j$. The dependence of $\Delta t_j$ on the dimension j corresponds to a different time offset between MEG samples for each dimension. This is evident in FIG. 1 as different time offsets between peaks of MEG cycles are shown for each dimension.

From the analytic form of the phase $\phi_n$ of each sample and in each dimension, as expressed in Equation (3), it is evident that referencing each MEG start time s of an MEG with zero phase onset to the time $t=0$ (or some other reference time) is equivalent to referencing instead an initial phase of value $$-2\pi j \frac{n}{N}$$

of the MEG in the jth direction and at the nth sample (i.e., a starting phase of the sinusoidal function representing the MEG in the jth direction and at the nth sample) to an initial reference phase $\Theta_{ref}$ of the mechanical vibration 102 at $t=0$ (or some other reference time). This equivalence is inherent in the mathematical properties of sinusoidal functions, and more generally in periodic functions that are symmetric about the time axis (e.g., periodic "bipolar" functions). In the example illustrated in FIG. 1, the initial reference phase $\Theta_{ref}$ of the mechanical vibration 102 is just the phase at $t=0$ of the sinusoid representing the mechanical vibration 102.

As illustrated in the example of FIG. 1, the start of all MEGs in the first time step ($n=0$) coincides with $t=0$. For example, application of SLIM-MRE in one demonstration configuration using $f=5$ kHz and 5 cycles of a sample slice thickness of one millimeter with TR/TE=200/6.94 ms, a field of view of 10×10 mm$^2$, a matrix size of 128$^2$, and flip angle=30%, simultaneous MRE data in all three dimensions was acquired using a SLIM-MRE duration was approximately 6.8 minutes. In comparison, conventional MRE experiments requiring three individual, sequential experiments, one for each direction, resulted in a compilation of the three dimensions of MRE data in an MRE imaging time of approximately 20.5 minutes. Application of SLIM-MRE in another demonstration configuration is described below, together with a discussion of the results.

In the SLIM-MRE demonstration configuration, the x-MEG 104 component in the x-direction used a sampling interval of 25 microseconds. The y-MEG 106 component in the y-direction used a sampling interval of 50 microseconds, and the z-MEG 108 component in the z-direction used a sampling interval of 75 microseconds. In conventional MRE and SLIM-MRE, two-dimensional local frequency estimation (LFE) was applied to the conventional and to the demonstration images, respectively, and the wave length images were averaged over the region of interest, which corresponded to the largest bead (test material) within the image slice.

By observing individual displacement components using different time discretization intervals in accordance with SLIM-MRE, the components can be modulated with different frequencies in the MR signal phase $\phi$, expressed as a harmonic function of the start time of the MEG. But in contrast to conventional 3D MRE, all displacement components are acquired faster in SLIM-MRE, and can be derived from the same temporally-resolved MR phase images without sacrificing the image quality.

As discussed below, complex wave images in the axial plane at 5 kHz acquired using conventional MRE and using SLIM-MRE may be compared. For both conventional MRE and SLIM-MRE, the wave amplitude was seen to vary for the different encoding directions. Amplitudes were the strongest for motion encoding in the z-direction for both conventional MRE and SLIM-MRE, as this was the principle direction of motion in the experimental setup. The bead (test object) x- and y-displacements for both the conventional MRE and SLIM-MRE were visible, and caused by transmission and reflection of wave energy at the spherical bead boundaries. Wave images corresponding to the same encoding direction were seen to be similar. Thus, independent of standard MRE and SLIM-MRE, the average LFE-derived wave length λ over the region of interest was (0.6±0.1) mm, (0.6±0.1) mm, and (0.5±0.1) mm for encoding in the x-, y- and z-direction, respectively.

2. Example Method

Embodiments disclosed herein by way of example of SLIM-MRE provide example techniques applicable in an MRI system that includes capabilities for applying motion encoding gradients (MEGs), and further includes a mechanism for inducing one or more forms of mechanical vibrations in an object under study in the MRI system. As described above, an MRI system typically comprises hardware components including one or more gradient coils positioned about a bore of a magnet, an RF transceiver system, and an RF switch controlled by a pulse module to transmit RF signals to and receive RF signals from an RF coil assembly. The received RF signals are also known as magnetic resonance (MR) signal data. An MRI system also typically includes one or more computers programmed to cause the system to apply to an object in the system various RF signals, magnetic fields, and field gradients for inducing spin excitations and spatial encoding in an object, to acquire MR signal data from the object, to process the MR signal data, and to construct an MR image of the object from the processed MR signal data. The one or more computers can include one or more general or special purpose processors, one or more forms of memory, and one or more hardware and/or software interfaces for interacting with and/or controlling other hardware components of the MRI system.

Figure 2:
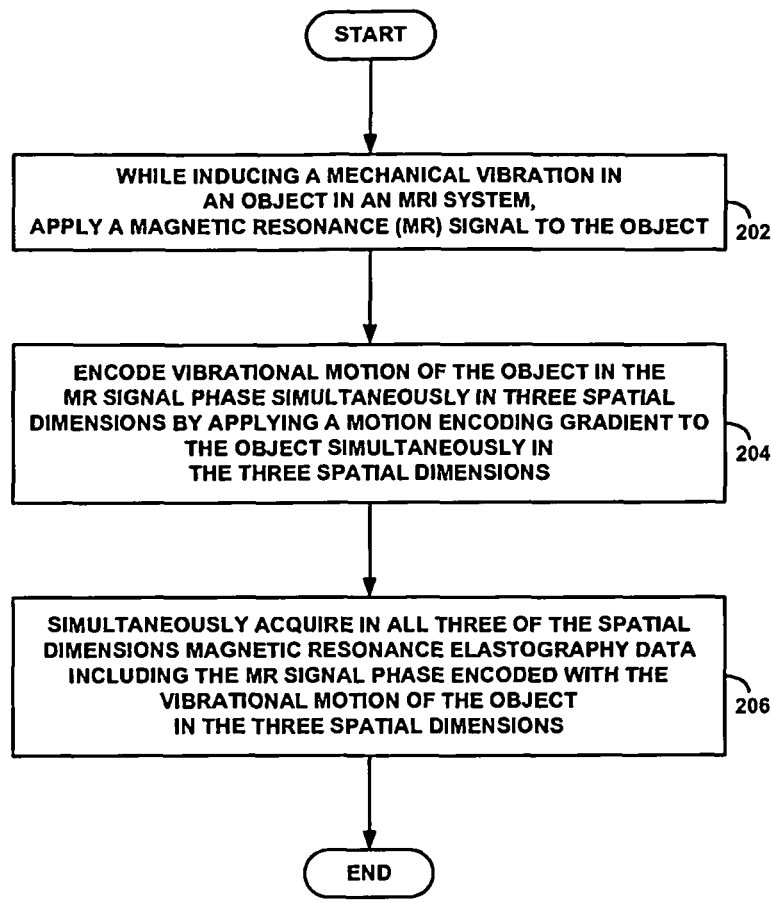
FIG. 2 is a flowchart depicting an example embodiment of sample interval modulation magnetic resonance elastography.

In an example embodiment, acquisition of MRE data simultaneously in three dimensions (3D) in accordance with SLIM-MRE can be accomplished by way of a computer-implemented method configured for execution by the MRI computer. The steps of the method can augment and/or enhance conventional MRI operation in order to achieve the advantages of SLIM-MRE. FIG. 2 is a flowchart illustrating an example method of SLIM-MRE applied to an object in an MRI system.

At step 202, the MRI system applies a MR signal to the object in the MRI system while a mechanical vibration is induced in the object. The MR signal may be characterized by one or more properties, including a phase, referred to herein as the "MR signal phase." Mechanical vibrations induced in the object may manifest as vibrations of the material of the object, and can be described analytically as time-dependent (e.g., period) physical displacements of the material in one or more spatial dimensions. An example mechanism for introducing mechanical vibrations in the object while it is subject to the MR signal is described below.

At step 204, the vibrational motion of the object is encoded in the MR signal phase simultaneously in three spatial dimensions by applying a motion encoding gradient (MEG) to the object simultaneously in the three spatial dimensions. Encoding the MR signal phase with vibrational motion yields a signal that carries time-dependent displacement information, which can be recovered and analyzed to determine mechanical properties of the material of the object. The motion-encoded MR signal phase is referred to herein as a "magnetic resonance elastography" (MRE) signal, and forms a basic element of what is referred to herein as MRE data. In accordance with example embodiments, the MRE signal is generated simultaneously in three spatial dimensions.

Finally, at step 206, all three of the spatial dimensions of the MRE data are acquired simultaneously. In doing so, the MR signal phase encoded simultaneously in the three spatial dimensions with the vibrational motion of the object is acquired. That is, in accordance with example embodiments, the three dimensions of MRE signal are generated simultaneously, and three dimensions of MRE data are acquired simultaneously. In further accordance with example embodiments, acquiring in all three of the spatial dimensions MRE data simultaneously can entail storing encoded vibrational motion in the three spatial dimensions in a same k-space.

In accordance with example embodiments, the three spatial dimensions can be taken to be three orthogonal spatial dimensions. In further accordance with example embodiments, the three orthogonal spatial dimensions can be taken to correspond to three Cartesian directions x, y, and z. In particular, x, y, and z can correspond to read, phase, and slice directions of the MM system.

In further accordance with example embodiments, a magnetic resonance elastogram can be generated from the simultaneously acquired MRE data. Because the MRE data are acquired simultaneously in three spatial dimensions, and include an MRE signal generated simultaneously in three dimensions, the magnetic resonance elastogram can be generated from MRE images of the vibration state in all three spatial dimensions that are aligned in space and in time.

Also in further accordance with example embodiments, the simultaneously acquired MRE data can be used to calculate a mechanical property of the object and/or of the material of the object. As an example, the mechanical property of the object can be shear and/or compression. More particularly, analysis of the simultaneously acquired MRE data could be used to separate shear from a compression wave in the object.

In accordance with example embodiments, applying the MEG to the object simultaneously in the three spatial dimensions to encode the vibrational motion of the object in the MR signal phase simultaneously in the three spatial dimensions (step 204) can entail simultaneously encoding a displacement in each of the three spatial dimensions of an isochromat in the MR signal phase. As noted above, the displacement in each of the three spatial dimensions can be a manifestation of the induced mechanical vibration in the object in each of the three spatial dimensions.

Also in accordance with example embodiments, applying the MEG to the object simultaneously in the three spatial dimensions to encode the vibrational motion of the object in the MR signal phase simultaneously in the three spatial dimensions (step 204) can entail acquiring the state of vibration in each dimension with a different sampling frequency. More particularly, the MEG can take the form of one or more MEG cycles of a periodic MEG applied over the course of a MEG application interval, and the MRE signal can be a harmonic function of a start time of a MEG application interval in each dimension. For example, applying the MEG to the object simultaneously in the three spatial dimensions can entail simultaneously applying a respective spatial component of the MEG in a respective temporal sequence of N MEG application intervals in each dimension. The start time of the MEG application interval in each dimension, measured with respect to a particular phase of the mechanical vibration, can be determined according to the dimension and an ordinal position of the given MEG application interval in the respective temporal sequence of the respective spatial component. The different start time in the different dimension can thus manifest as different sampling frequencies in the different spatial dimensions, and the MR signal phase can be encoded with a vibrational displacement in the respective dimension over a time duration of each MEG application interval in each respective dimension.

By way of example, each sequence of MEG application intervals can have a length of N=8 for all three spatial dimensions. It will be appreciated that other sequence lengths can be used. In conventional MRE application in which the MRE data are generated and acquired in only one dimension, or only one dimension at a time of multiple dimensions, a value of N≥8 is sometimes adopted as a practical matter.

In further accordance with example embodiments, the time duration of each MEG application interval could be the same, and the arithmetic difference between MEG start times of successive MEG application intervals for each respective spatial component could correspond to a respective sampling interval for the respective spatial component. The modulated sampling frequency could then be determined as the arithmetic inverse of the respective sampling interval for the respective spatial component. With this arrangement, encoding in the MR signal phase a vibrational displacement along all three spatial dimensions could correspond to determining an encoded MR signal phase for each of N samples.

More specifically, taking n=0, 1, . . . , N−1, the encoded MR signal phase of the nth of the N samples can be expressed analytically as:

$$\phi_n = \sum_{j=1}^{3} \varphi_j(s_{jn}) = \sum_{j=1}^{3} \xi_j u_j^0 \sin\left(2\pi j \frac{n}{N} + \Theta_j + \frac{\pi}{2}\right).$$

As discussed below in more detail, this expression can be derived from a basic equation of MRE for a case of simultaneously applied MEG components, with the respective sampling interval in the jth spatial component, j=1, 2, 3, given by $$\Delta t_j = \frac{j}{fN}.$$

In accordance with example embodiments, the MEG start time for each sample in each dimension, measured with respect to the particular (direction-dependent) phase of the mechanical vibration, may be expressed as $s_{jn}=n\Delta t_1$, n=0, 1, . . . , N−1. In the above expression for encoded MR signal phase $\phi_n$, $u_j^0$ is the displacement amplitude in the jth spatial component, $\xi_j$ is an encoding efficiency in the jth spatial component, and $\Theta_j$ is an initial phase of the mechanical vibration in the jth spatial component with respect to a reference time t=0.

In further accordance with example embodiments, simultaneously acquiring in all three of the spatial dimensions MRE data including the MR signal phase encoded with the vibrational motion of the object in the three spatial dimensions can then correspond to applying a discrete Fourier transform to $\phi_n$ to decompose individual components of displacement encoded in the MR signal phase.

It will be appreciated that the example method steps of the example embodiment of SLIM-MRE can be embodied as executable instructions stored on a non-transitory computer-readable medium, such as magnetic disk, CD-ROM, or the like. It will also be appreciated that the method steps described above can be modified or rearranged, and that additional steps can be added, without changing the scope or spirit of the example embodiment or other SLIM-MRE embodiments.

3. Example Analytical Description

Without being limited to any theory of the underlying basis for the invention one of ordinary skill will appreciate the following features of the MRE methods set forth herein.

The basic equation of MRE is represented by an integral over time (Muthupillai R, Lomas D J, Rossman P J, Greenleaf I F, Manduca A, Ehman R L: Magnetic resonance elastography by direct visualization of propagating acoustic strain waves. *Science* 1995, 269(5232):1854-1857), which describes the accumulation of the MR signal phase φ as a result of a harmonic vibration u of a tissue voxel (or test object voxel) while exposed to a magnetic field gradient G:

$$\phi = \gamma \int_0^T G(t) \cdot u(t) dt. \quad (4)$$

In Equation (4), γ and T correspond to the gyromagnetic ratio and the duration of the applied MEG, respectively. Without loss of generality, the gradient and vibration can be written as functions of the variable of integration t only, although G and u can also exhibit a dependency on frequency and initial phase. It is convenient to reformulate Equation (4) with the start time s of the MEG relative to a fixed origin of the time axis:

$$\phi(s) = \gamma \int_s^{s+T} G(t) \cdot u(t) dt. \quad (5)$$

The harmonic vibration is expressed with amplitude $u_0$, initial phase Θ and frequency f, and it can be assumed without loss of generality that the motion encoding gradients are also sinusoidal with frequency f, amplitude $G_0$, and initial phase $\Theta_M$. The vibration and gradient directions can be defined by the unit vectors $e_u$ and $e_M$, respectively, so that:

$$u(t) = u_0 \sin(2\pi ft + \Theta) e_u, \quad (6)$$

$$G(t) = G_0 \sin(2\pi ft + \Theta_M) e_M. \quad (7)$$

Magnetic field gradients with zero moment can be used as the MEGs in order to eliminate phase portions due to stationary spatial offsets. In this case, the MEG duration T corresponds to an integer multiple of the MEG periods (MEG cycles) 1/f.

$$T = \frac{M}{f}, M \in \mathbb{N}. \quad (8)$$

For purposes of the discussion herein, the duration T is also referred to as the "MEG application interval."

In the case of sinusoidal MEGs with zero phase at the start t=s of the MEG, the initial phase of vibration becomes:

$$\Theta_M = -2\pi fs. \quad (9)$$

A general solution of the integral equation (5) may be obtained using Equations (6)-(8):

$$\phi = \phi_0 \cos(\Theta - \Theta_M), \text{ with } \phi_0 = \frac{\gamma G_0 M}{2f} e_u \cdot e_M, \quad (10a)$$

while consideration of the case described by equation (9) yields:

$$\phi(s) = \phi_0 \cos(2\pi fs + \Theta), \text{ with } \phi_0 = \frac{\gamma G_0 M}{2f} e_u \cdot e_M. \quad (10b)$$

Equation (10b) can be considered as establishing that the MR phase φ, expressed as a trigonometric function of the MEG start time s, corresponds to a harmonic oscillation with the same frequency as the applied acoustic vibration. Therefore, the initial phase Θ and the amplitude $u_0$ of the vibration can be calculated by resolving φ with respect to s. In the general case of Equation (10a), Θ and $u_0$ can be determined by varying the phase difference between Θ and $\Theta_M$. This also holds when other balanced (zero moment) gradients are used, e.g., MEGs with a cosine or trapezoidal shape, and even when the MEGs oscillate with a frequency different from the vibration frequency. When applying these alternate forms of MEGs, only the encoding efficiency $$\xi = \frac{\phi_0}{u_0}$$

needs to be adjusted and the corresponding phase shift established as in Equations (10a) and (10b).

The MR phase φ is read in N discrete steps Δt for temporal resolution. This enables the Fourier transform U(f) of the real-valued displacement u(t) to be determined at the discrete frequencies (Oppenheim A V, Schafer R W: Discrete-time signal processing. Englewood Cliffs, N.J.: Prentice Hall; 1989)

$$n\Delta f = \frac{n}{N\Delta t}, n = 0, 1, \ldots, \frac{N}{2} - 1. \quad (11)$$

In conventional MRE, the MEG is shifted over the period 1/f of the vibration frequency using a sampling interval Δt=1/(Nf). Consequently, the spectral value of U(nΔf) is stored into the first frequency component (n=1). While an MRE approach based on multifrequency fractional motion encoding (Klatt D, Hamhaber U, Asbach P, Braun J, Sack I: Noninvasive assessment of the rheological behavior of human organs using multifrequency MR elastography: a study of brain and liver viscoelasticity. *Physics in medicine and biology* 2007, 52(24):7281-7294) makes use of the spectral values at n>1, these higher order frequency components are typically discarded in conventional mono-frequency MRE. For the acquisition of all components of the displacement vector according to conventional MRE methods, the above procedure is repeated three separate (consecutive) times, while applying the MEG in mutually orthogonal directions in the consecutive steps (Glaser K J, Manduca A, Ehman R L: Review of MR elastography applications and recent developments. *J Magn Reson Imaging* 2012, 36(4):757-774).

By contrast, in SLIM-MRE, the amplitudes and the initial phases of the displacement projections, which are different for the three spatial directions and are therefore denoted with $u_{0,j}$ and $\Theta_j$ in the following, can be calculated from the discrete MR phase in only one temporally-resolved MRE experiment. In this approach, the MEGs corresponding to the three spatial directions are applied simultaneously, but with different sampling intervals for the phase shift of the MEG and the respective vibration projection. The theoretical basis of SLIM-MRE may be derived by adapting the MR phase in Equation (5) to a function of three variables ($s_1$, $s_2$, $s_3$) representing the start times of the x-, y- and z-MEGs:

$$\phi(s_1,s_2,s_3) = \gamma \Sigma_{j=1}^3 \int_{s_j}^{s_j+T} G_j(t) \cdot u_j(t) dt. \quad (12)$$

In this expression, the x-, y- and z-directions are indexed by j=1, 2, 3. In accordance with example embodiments of SLIM-MRE, MEGs with zero phase at their onset and fixed, common duration T are used, while the MEG start times are varied. The solution from Equation (10b) may be adopted by taking into account direction-specific MEG amplitudes $G_{0,j}$:

$$\phi(s_1, s_2, s_3) = \sum_{j=1}^{3} \phi_{0,j} \cos(2\pi f s_j + \Theta_j), \quad (13)$$

with $\phi_{0,j} = \frac{\gamma G_{0,j} M}{2f} u_{0,j}$.

In accordance with example embodiments of SLIM-MRE, modulation of the sampling intervals $\Delta t_j$ with respect to the x-, y- and z-directions are considered. For only MEGs with zero phase at their onset, the resulting direction-specific, discrete start times $s_{jn}$, can be written as $$\Delta t_j = \frac{j}{Nf}, s_{jn} = n\Delta t_j, n = 0, 1, \ldots, N-1; j = 1, 2, 3. \quad (14)$$

Equation (14) can be considered as corresponding to the x-, y- and z-MEGs being shifted over one, two and three times the vibration period, respectively. It will be appreciated that this order can also be permuted. The discretization of φ can be obtained by inserting Equation (14) into Equation (13):

$$\phi_n = \sum_{j=1}^{3} \phi_{0,j} \cos\left(2\pi \frac{jn}{N} + \Theta_j\right), \text{ with } \phi_{0,j} = \frac{\gamma G_{0,j} M}{2f} u_{0,j}. \quad (15)$$

Figure 3:
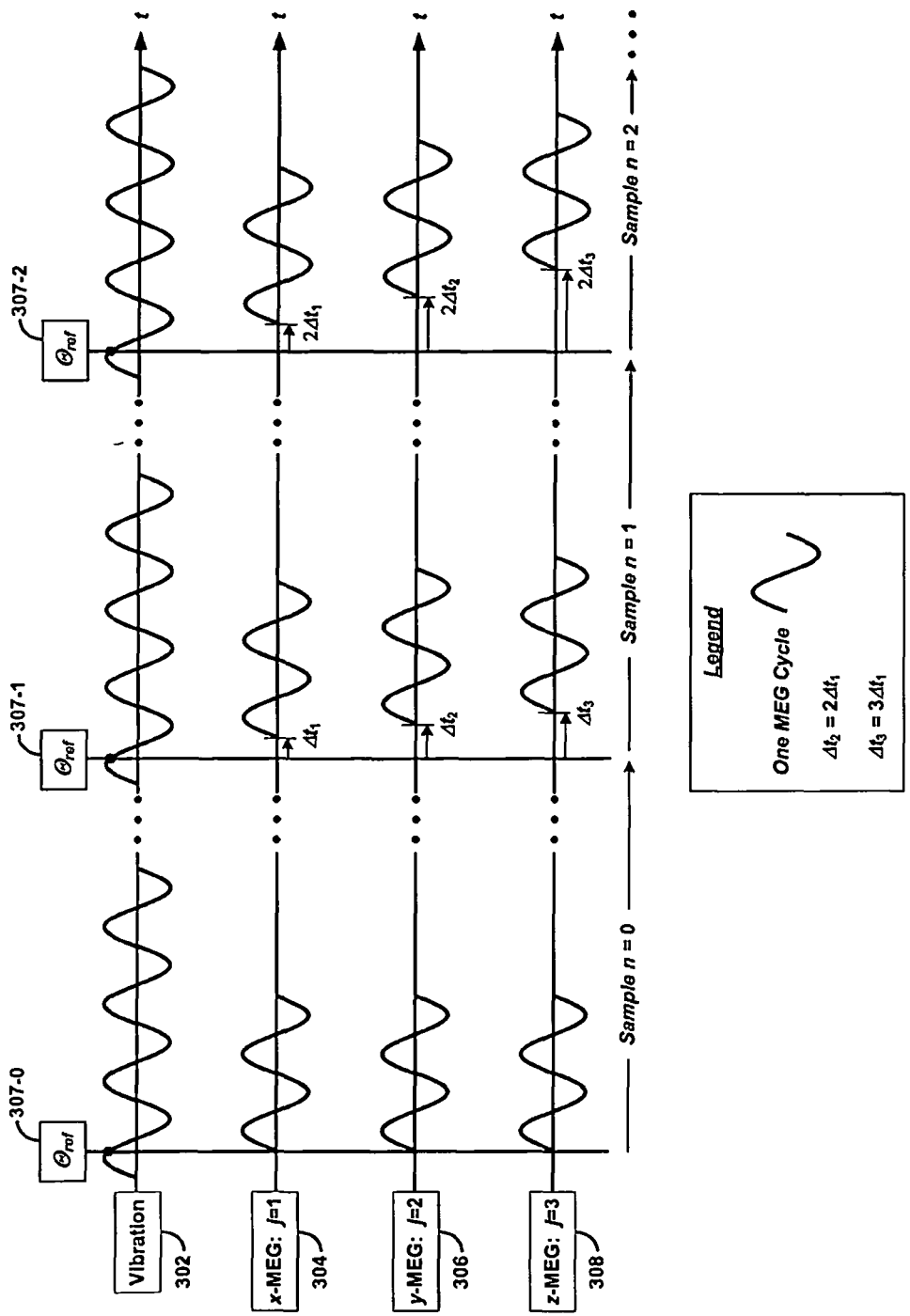
FIG. 3 illustrates simultaneous application of three spatial components of magnetic encoding gradients for a subset of samples, in accordance with an example embodiment.

FIG. 3 shows a "decomposed" version of the example MEG arrangement illustrated in FIG. 1 in which the overlapped samples in FIG. 1 are now separated in time, and two MEG cycles are depicted for each component dimension and each sample (the Legend in FIG. 3 shows one MEG cycle). For purposes of illustration, only the n=0, 1, and 2 of the N=8 samples are shown (where n=0, 1, . . . , N−1=7 for the present example). All three of the eight samples shown in FIG. 3 are referenced to the same reference phase $\Theta_{ref}$ of the mechanical vibration 302. At each sample in FIG. 3 only one of the three vibration projections is shown. Since the offsets of the initial phases ($\Theta_2-\Theta_1$), ($\Theta_3-\Theta_1$), and ($\Theta_3-\Theta_2$) are constant at each sample, the shifting of the MEG can be illustrated with respect to one vibration with initial phase $\Theta_{ref}$ which can be any of the three $\Theta_j$. Specifically, and by way of example, the sample n=0 begins at $\Theta_{ref}$ 307-0; the sample n=1 begins at $\Theta_{ref}$ 307-1; and the sample n=2 begins at $\Theta_{ref}$ 307-2. As illustrated in FIG. 3, the n=0 sample of the x-MEG 304 begins at (n=0)·Δt$_1$=0 from the time corresponding to $\Theta_{ref}$ 307-0. Similarly, the n=0 samples of the y-MEG 306 and the z-MEG 308 begin at (n=0)·Δt$_2$=0 and (n=0)·t$_3$=0, respectively, from the time corresponding to $\Theta_{ref}$ 307-0. In accordance with Equation (14), and as indicated in the Legend in FIG. 3, Δt$_2$=2Δt$_1$ and Δt$_3$=3Δt$_1$.

For the n=1 samples, the respective MEG start times of the x-MEG 304, y-MEG 306, and z-MEG 308 are shifted with respect to the time of →$_{ref}$307-1 by Δt$_1$, Δt$_2$=2Δt$_1$, and Δt$_3$=3Δt$_1$, respectively. For the next sample, n=2, the respective MEG start times of the x-MEG 304, y-MEG 306, and z-MEG 308 are shifted with respect to the time of $\Theta_{ref}$ 307-2 by 2Δt$_1$, 2Δt$_2$=4Δt$_1$, and 2Δt$_3$Δ=6Δt$_1$, respectively. This iteration of MEG start times repeats up through n=N−1.

Figure 4:
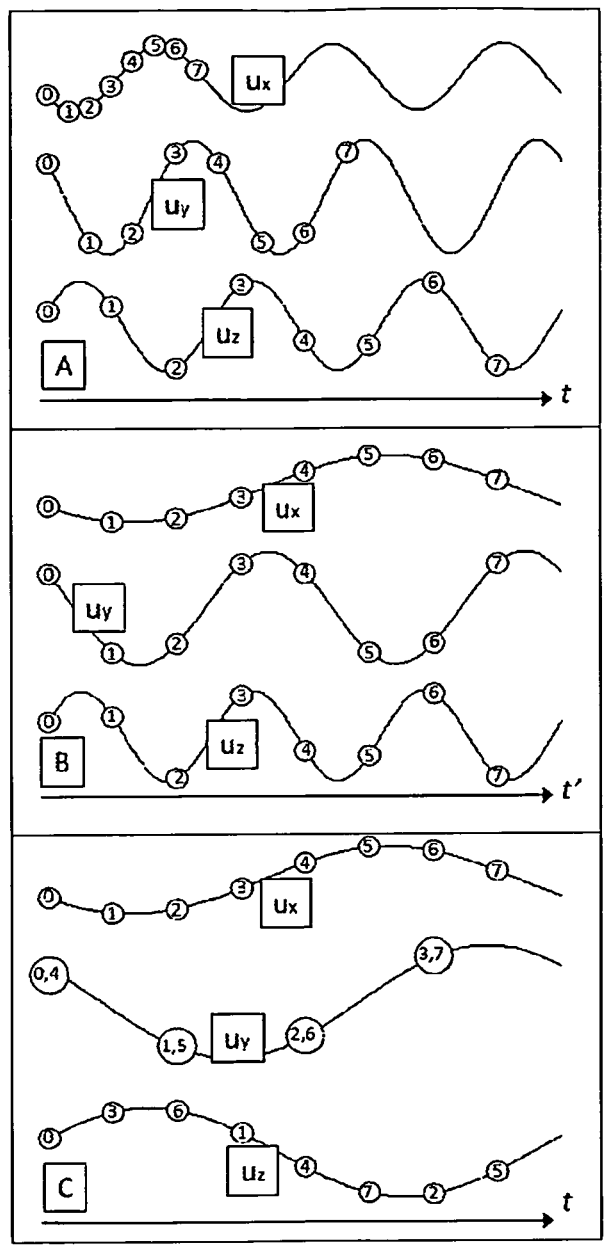
FIG. 4 illustrates a relationship between displacement and movement encoding gradients, in accordance with an example embodiment.

Equation (15) corresponds to the first three summands (neglecting the DC component) of a discrete Fourier series in amplitude-phase notation (Oppenheim A V, Schafer R W: Discrete-time signal processing. Englewood Cliffs, N.J.: Prentice Hall; 1989). It can be observed from Equation (15) that the modulation of the sample interval, as described by equation (14) encodes the amplitude $u_{0,j}$ and the initial phase $\Theta_j$ of the x-, y- and z-projection of the displacement with different "apparent" frequencies into the discrete MR phase $\phi_n$, specifically with the first, second, and third harmonics, respectively. The described relationship is depicted in FIG. 4, panels A and B. Specifically, FIG. 4 illustrates the relation between the displacement projections $u_x$, $u_y$, and $u_z$ (solid lines) and the MEG start times (circles) of the respective MEG components. The numbers within the circles correspond to the discrete time step n as defined in Equation (14).

Panel A at the top of FIG. 4 depicts the encoding in real time t, without accounting for periodicity. In panel B (middle of FIG. 4), the accumulated MR phase portions of the projections are summed up at each sample in accordance with Equation (15). The effect is that in the discretized time domain t' of synchronous sampling instances, the three projections exhibit distinct different frequencies. Consequently, amplitude and phase of each projection can be obtained from the Fourier transform of the discrete MR phase.

Because of Equation (11), the acquisition of eight samples (N=8 for the example embodiment under discussion) is sufficient to decompose the three projections by applying a discrete Fourier transform to $\phi_n$.

A periodicity relation can be read from Equation (15) in terms of a replacement of the factor jn/N with the modulo value of jn/N, yielding the same result for $\phi_n$. Consequently, the start of the MEGs as described in Equation (14) can be earlier due to periodicity, $$s_{jn} = \frac{1}{f}\text{modulo}\left\{\frac{jn}{N}, 1\right\}, n = 0, 1, \ldots, N-1. \quad (16)$$

Equation (16) represents a useful property for minimizing the increase in echo time TE due to the delays in the application of the MEGs, which can be a side effect of the MEG start times, while accounting for their overall periodicity. This is illustrated in FIG. 4, panel C (bottom), which depicts the encoding in real time t, but now accounting for the periodicity described by Equation (16).

4. Example Operation and Results

The following discussion describes an example embodiment of SLIM-MRE implemented in a MRI system, as well as an example SLIM-MRE procedure carried out using a test object. Results of the example procedures are discussed in a subsequent section.

a. Demonstration System and Example Procedure

A demonstration SLIM-MRE procedure was carried out at 5 kHz using a vertical bore μMRE/MRI system (described in Klatt D, Yasar, T K, Royston T J, Magin R L, Sample interval modulation for the simultaneous acquisition of displacement vector data in magnetic resonance elastography: theory and application. *Physics in Medicine and Biology* 2013, 58: 8663-8675). It will be appreciated that the technique is independent of the specific mechanical frequency, and can be implemented on any MRI system configured to collect MRE phase images.

Experimental Setup

Experiments were performed in an 11.7 Tesla vertical bore Broker MRI system having an inner diameter (ID) of 56 mm. A saddle RF coil (ID=10 mm) was used with micro imaging gradient coils (ID=19 mm) and 300 Gauss/cm maximum gradient field per direction. This system can be considered a specific example of a generic MRI system, such as one described above in the Background section herein.

As a test object, an inhomogeneous sample composed of an agarose bead embedded in agarose gel formed from a different concentration was used in all experiments. For the experimental arrangement of the demonstration system, it was possible to generate displacements in all three spatial dimensions within the image slice due to the reflection and refraction of the mechanical energy at the spherical bead surface.

A vibration device including a piezoelectric actuator (6.5 mm×6.5 mm×18 mm, Thor Labs Inc.) was used to induce mechanical vibrations in test samples, in accordance with SLIM-MRE procedures described above. More particularly, samples were placed in a plastic test tube, which was attached to the piezoelectric actuator. At the other end of the piezoelectric actuator, a counter mass was placed to provide an inertial ground. It should be understood that example embodiments of SLIM-MRE are not limited to using the particular form of vibration device used in the demonstration system and described herein.

Figure 5:
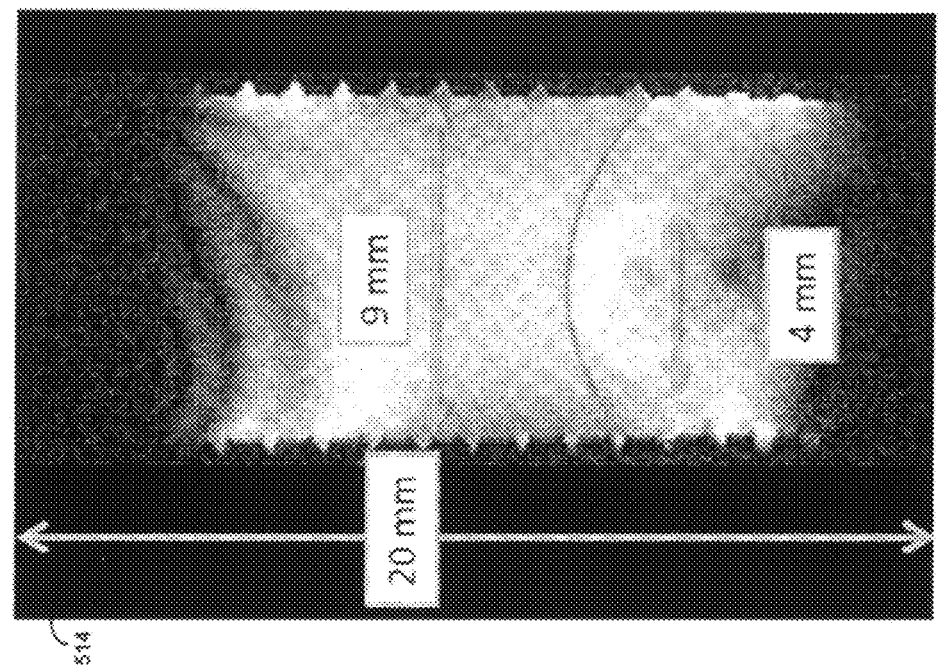
FIG. 5 shows a vibration device, in accordance with an example embodiment.
Figure 5:
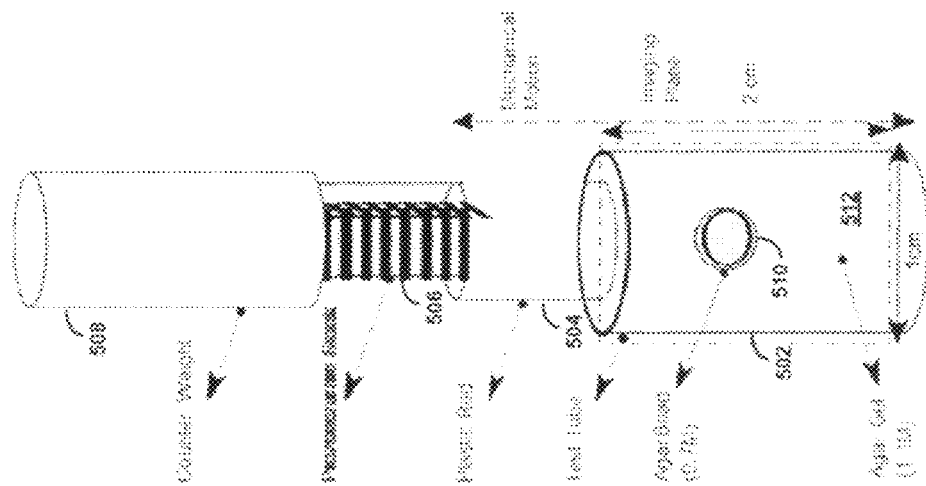

The vibration device is shown in FIG. 5, together with a test conventional MRI image. The mechanical actuation setup inside the vertical 11.7 T MRI system is depicted on left. A test tube 502 is attached by a plastic rod 504 to the piezoelectric actuator 506, which in turn is connected to the counter mass 508. The test object in the demonstration study includes an agarose bead 510 immersed in an agarose gel 512 within the test tube 502. As shown in the Figure, the test tube 502 had a diameter of 1 cm and a height of 2 cm. Mechanical vibrations were induced along the height of the test tube 502 and in the imaging plane, as indicated by the double-ended arrows in the left side of FIG. 5.

A magnitude image of the test sample from conventional MRE acquisition using the demonstration system is shown on the right side of FIG. 5. The inner wall of the test tube 502 was threaded to provide better traction between the agarose gel 512 and the test tube 502. A dark arc seen in the magnitude image close to the agarose bead 510 is a result of the sample preparation process. Specifically, the agarose gel 512 was cured in two steps. First, the upper part was poured (while the test tube 510 was upside down) and cured to prevent the agarose bead to sink. Then in the second step, the bottom part was poured in. The dark arc in the image corresponds to the contact surface of the two layers.

A harmonic mechanical vibration of 5 kHz frequency was introduced into the sample by driving the piezoelectric actuator with a power amplifier. The amplifier signal was biased by a DC supply to prevent a negative voltage, which can be damaging to the integrity of the piezoelectric actuator. Axial symmetry of the experimental configuration of the actuator caused geometric focusing of the induced mechanical waves within the sample. This superposition and convergence of wave fronts thus compensates for the strong damping of shear waves at 5 kHz in soft biological tissues and in tissue-like phantoms (Yasar T, Royston T J, Magin R L: Wideband MR elastography for viscoelasticity model identification. *Magn Reson Med* 2013, 70:479-489; Royston T J, Yasar T K, Magin R L: Geometric Focusing of High Frequency Shear Waves for Noninvasive High Resolution MR Elastography. In: *Proc 19th Annual Meeting ISMRM*. Montreal; 2011: 3481).

Sample Preparation

The test tube 502 was a cylindrical plastic container (height=20 mm; ID=9 mm). The sample was composed of an agarose bead 510 (0.7% by water) with diameter 4 mm submerged in agarose gel 512 (1.1% by water). The sample was freshly prepared one day before the experiment and stored overnight in the MRI room at 20° C.

Image Acquisition

A fast spin echo-based pulse sequence was used for data acquisition. Sixteen sagittal slices were obtained with the following imaging parameters: repetition time TR=1500 ms; effective echo time TE=23 ms, echo number 4; field of view (FOV)=20 mm×10 mm; slice thickness=0.5 mm; matrix size=256×128; MEGs with 20% of full power were placed in read, phase and slice directions. While eight time steps were used in all three directions, the sampling interval was different for each direction in accordance with SLIM-MRE. Periodicity was accounted for with respect to the start of the MEG relative to the vibration (see Equation (16)). Results are discussed below with reference to FIGS. 6 and 7.

The MEG onsets in the demonstrations study are shown in FIG. 8, table 802, which lists three columns (i), (ii), and (iii) for each component j=1, 2, 3. Column (i) for each j lists the MEG start times according to Equation (14), without accounting for periodicity. This corresponds to the example illustrated in panels A and B of FIG. 4. Column (ii) for each j lists the MEG start times according to Equation (16), this time accounting for periodicity. This corresponds to the example illustrated in panel C of FIG. 4. Column (iii) for each j lists the numerical values of MEG start times used in the demonstration system as described herein (i.e., column (ii) with $\frac{1}{8}$f=25 μsec, or 1/f=200 μsec).

At each time step, two acquisitions were conducted with inverse MEGs to calculate phase-difference images for clearing biases originating from static magnetic field inhomogeneity. The duration of SLIM-MRE acquisition was ~12.8 min. For comparison, conventional MRE experiments were performed, in which the three components of the displacement vector were acquired in three individual experiments consecutively, resulting in a total measurement time of ~38.4 min. In both conventional and SLIM-MRE, 2D local frequency estimation (LFE) was applied to the images (Knutsson H, Westin C J, Granlund G: Local multiscale frequency and bandwidth estimation. In: *Proc of the IEEE Intl Conf on Image Processing:* 1994; 1994: 36-40) for determination of the wave length $\lambda$. Elastograms representing the stiffness p were calculated using $\mu=\rho(\lambda f)^2$, while assuming a density of $\rho=1000$ kg/m$^3$. Finally, the stiffness was averaged over the region of interest (ROI), which corresponded to the bead within the image slice. An experimental uncertainty ("error") was determined in terms of the standard deviation (SD).

b. Illustrative Results

Figure 6:
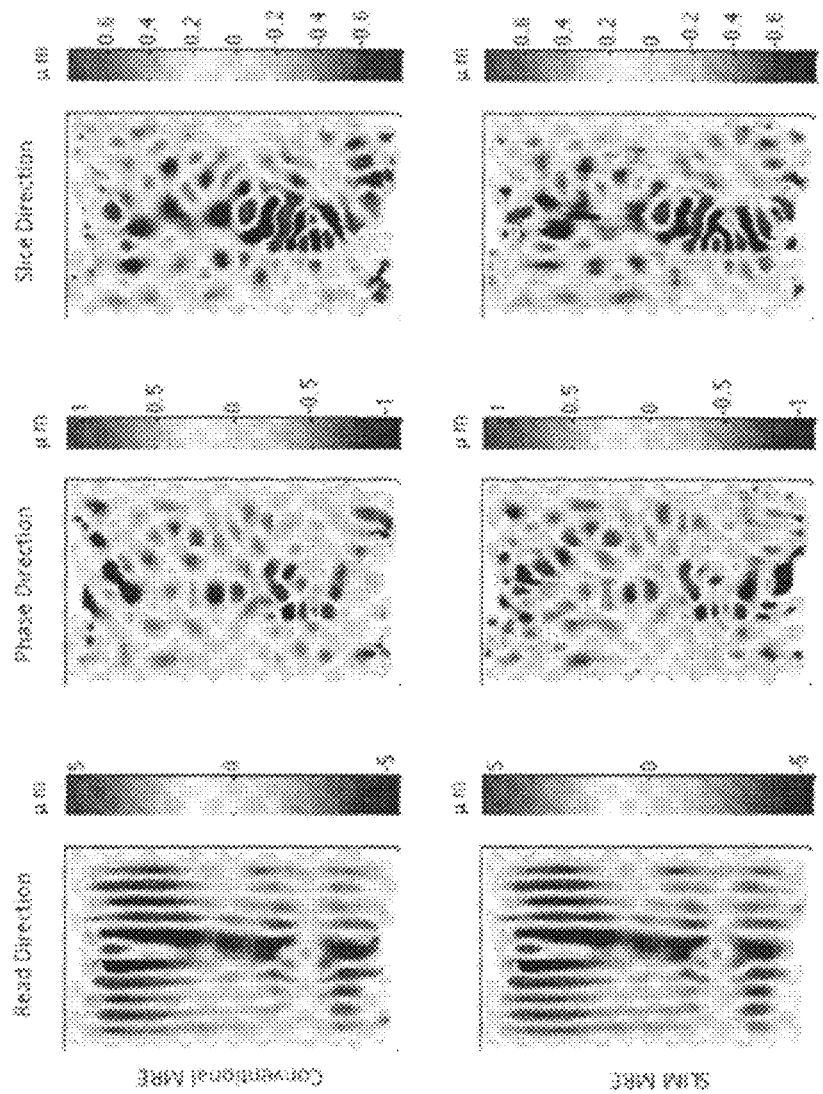
FIG. 6 shows MRE images for both conventional MRE and SLIM-MRE, in accordance with an example embodiment.

SLIM-MRE was successfully implemented and applied to the test sample object, also sometimes referred to customarily as a "phantom" in MRI studies. In FIG. 6 the complex wave images of the three displacement components are illustrated in an image slice, which intersects the bead and is parallel to the MRI axis. Images obtained using conventional MRE in consecutive acquisition blocks (top row) are compared to the results of SLIM-MRE (bottom row). In FIG. 6, one displacement component is shown per column, as indicated in the heading.

In both image sets of FIG. 6, the wave amplitude was seen to vary for each of the different encoding directions. Even though the wave amplitudes are the highest in z-direction (read direction), as the piezoelectric actuator introduced motion along the longer axis of the imaging slice, x and y-displacements are also clearly visible within the bead. These components resulted from refraction and reflection of wave energy at the spherical bead boundaries. It is evident from visual comparison of the SLIM-MRE and the conventional MRE that the wave images corresponding to the same encoding direction exhibit similar wave structures.

Figure 7:
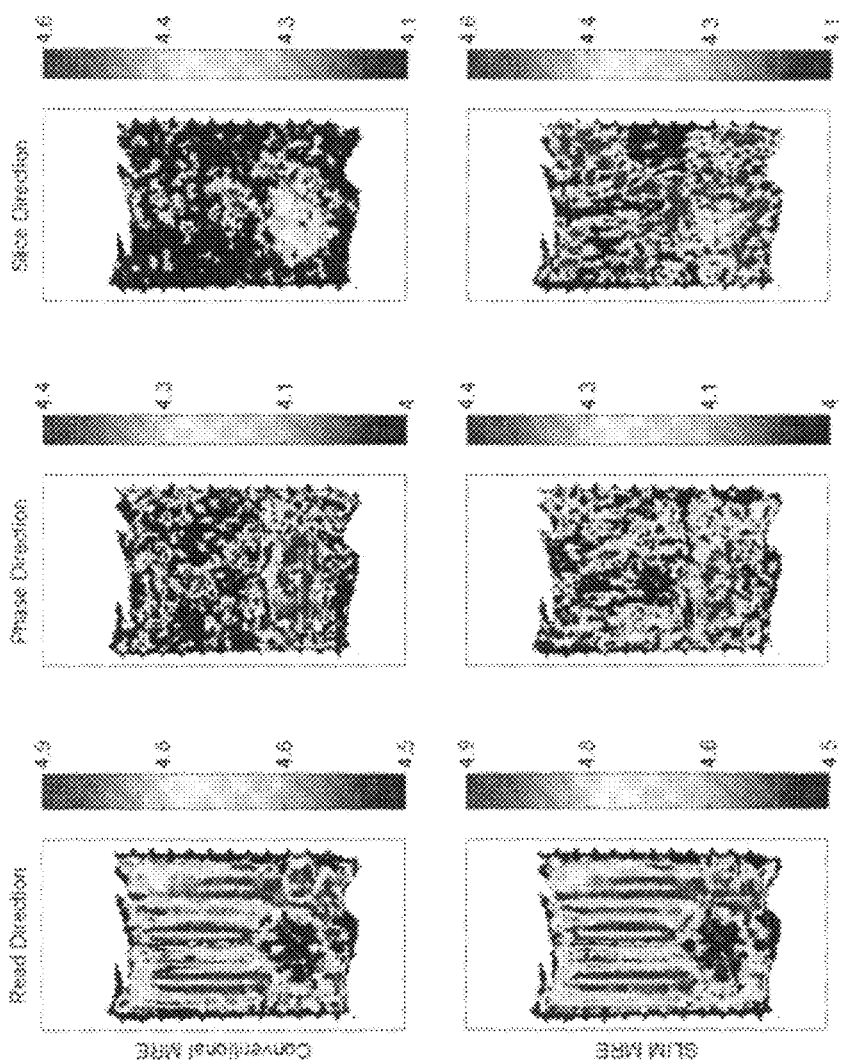
FIG. 7 shows elastograms for both conventional MRE and SLIM-MRE, in accordance with an example embodiment.

FIG. 7 shows the LFE-derived elastograms calculated from the wave images in FIG. 6, which were acquired consecutively using conventional MRE (top row) and simultaneously using SLIM-MRE (bottom row). Elastograms with respect to one displacement component are shown per column as indicated in the heading. The position of the bead is indicated, while the best delineation of the bead from the surrounding is visible in the read-direction. Using SLIM-MRE the stiffness values averaged over the bead were 33.5±9.3 kPa, 22.0±6.3 kPa and 23.3±8.2 kPa for the read-, phase- and s/ice-component, respectively. By comparison, using conventional MRE, the stiffness values averaged over the bead were 33.0±9.7 kPa, 23.1±5.0 kPa and 24.1±4.9 kPa for the read-, phase- and s/ice-component, respectively.

As shown herein, example embodiments of SLIM-MRE enable acquisition of all three motion components of a single frequency vibration simultaneously. In the demonstration system, the use of eight samples for temporal resolution was sufficient to decompose the three displacement components, which were encoded with different discrete frequencies in the MR signal phase. Accordingly, SLIM-MRE is faster than conventional motion encoding techniques, where four to eight samples are acquired for each component. Since SLIM-MRE is capable of acquiring all components of the 3D displacement vector simultaneously, the technique can be more accurate than conventional motion encoding approaches, where the three projections of the displacement are acquired consecutively in individual experiments. Accordingly SLIM-MRE can also reduce or eliminate the susceptibility of conventional MRE techniques to image mis-registration artifacts generated over time and due to biological motions or different physiological states.

Results from applying SLIM-MRE example operation with the demonstration system using an inhomogeneous agarose phantom are comparable to conventional MRE, with similar wave images and the same LFE-derived stiffness values, within the error margins. The delineation of the bead from the surrounding gel is most distinct for the read direction, which represents the principle direction of vibration in our setup. While the refraction of shear waves resulted in vibration also along the phase and slice direction within the bead, there was no significant motion visible for these components in the surrounding gel except within the vicinity of the bead. It is inherent to the LFE-technique that the wave motion outside the bead also contributes to the estimated wavelength within the bead. Hence, the standard deviation (SD) of the stiffness within the bead is the highest for the read direction.

In the example operation, there was no consistent trend in stiffness and SD differences for the individual motion encoding directions between conventional MRE and SLIM-MRE. While the LFE-derived stiffness values were the same within the error margins using both approaches, some reason for the measured differences may be suggested. Concomitant field terms, which are typically present with non-linear spatial dependence, play a role when a linear gradient is activated (Bernstein M A, Thou X H J, Polzin J A, King K F, Ganin A, Pelc N J, Glover G H: Concomitant gradient terms in phase contrast MR: Analysis and correction. *Magn Reson Med* 1998, 39(2):300-308). In conventional MRE, these terms are imaged on the DC component for a static voxel and on the second harmonic for a vibrating voxel, and thus do not generally interfere with the complex wave image of interest. In SLIM-MRE the second harmonic frequency bin is used for the encoding of one vibration direction and the concomitant field terms can potentially interfere. However, using the first order approximation of the concomitant field given in (Bernstein M A, Zhou X H J, Polzin J A, King K F, Ganin A, Pelc N J, Glover G H: Concomitant gradient terms in phase contrast MR: Analysis and correction. *Magn Reson Med* 1998, 39(2):300-308), it can be assessed for the demonstration system configuration that the ratio of the concomitant field to the field induced by the gradients is only on the order of 0.8%. Therefore the expected error can be expected to be below the noise level. Also, the concomitant field effects in MRE are removed in phase-difference images calculated from acquisitions with inverse MEG polarities, as was done in the example operation.

As noted, the demonstration system and example operation used fast spin-echo MR sequence upgraded with motion encoding gradients according to the SLIM-concept. Eight time steps were acquired and the displacement projections were determined for three mutually orthogonal directions that are defined by the gradient coils. It will be appreciated that SLIM-MRE techniques can be extended to more than three directions, given a sufficient number of time steps. SLIM-MRE techniques can also be applicable to any combination of directions. Further, SLIM-MRE is not bound to a specific sequence type, but is applicable to all standard sequences commonly used in MRE, such as spin-echo, gradient-echo, EPI, and spiral based pulse sequences.

In standard MRE approaches, the start of the vibration is typically shifted relative to the RF pulse, which leaves the MEGs unchanged in individual time steps with respect to the sequence timing. This is different from SLIM-MRE, where the direction-dependent MEG start times can increase the minimum echo time. In the example operation described above, the timing of the vibration relative to the RF pulse was not changed. Rather, temporal resolution was achieved solely by adjusting the MEG timing. Using this approach, the TE has to be increased by 87.5% of the MEG period. This is due to the fact that 7/(8f) corresponds to the latest MEG start time when accounting for periodicity (see FIG. 8). It can be noted that the TE-prolongation can be further reduced. For this purpose, as a first step, the interval between the RF pulse and the earliest start time at each n can be constant, and consequently the vibration can to be shifted with respect to the earliest start time. The TE-increase then accounts for only 62.5% of the MEG period, since the maximum difference between the start times of different MEGs at the same n is equal to 5/(8f), as can be seen in table 802 of FIG. 8 for the case of periodicity. Then as a second step, a symmetry of the phase integral (Equation (5)) can be exploited. Its solution (Equation (10b)) remains unchanged, when the MEG is inverted and its onset is brought forward by half a vibration period. Thus the TE increase can further be reduced to 25%. Some degree of TE-prolongation can be expected to be unavoidable using MEGs with zero phase onset.

While there can be increase of the minimum echo time of SLIM-MRE compared with conventional MRE, this effect is less relevant in high field, small scale scanners, where multiple MEG cycles are typically applied. In these cases, the SLIM-related prolongation of TE can account for only a fraction of the total MEG duration, which was 17.5% in the demonstration system and example operation discussed herein (because of the use of five MEG cycles per direction and sample). In human studies, however, various MRE protocols use only one MEG cycle, which can result in a TE-increase of 25% of the MEG duration period, when using MEGs with zero phase onset in SLIM-MRE. The effect of decreased signal to phase ratio due to prolonged TE can be compensated for by the use of simultaneous, rapid acquisition in SLIM-MRE.

In accordance with example embodiments of SLIM-MRE, multidirectional data can even be acquired without increasing the minimum TE compared to conventional MRE. In this case the simultaneous acquisition of all components of the displacement vector can require the sampled MEG start phase to be direction-dependent. This approach would account for temporal resolution by varying the phase $\Theta_M$ of the MEG at its start time (Equation (10a)) and not by shifting the start s of the MEG the vibration relative to the vibration (Equation (10b)). While mathematically equivalent with respect to the modulation of the sample interval, the applied MEGs might possess different gradient moment nulling characteristics at the temporally-resolved images. More precisely, the displacement projection at one sample might be flow-compensated using a cosine-shaped MEG, flow-uncompensated using a sinus-shaped MEG or a mixture of both, when the MEG start phase is neither zero, nor a multiple of $\pi/2$.

A comparison of SLIM-MRE and conventional MRE on an inhomogeneous gel sample using a high field vertical MRI system gave the same LFE-derived stiffness values within the error margins, while reducing the necessary number of temporally-resolved MRE experiments from three to one.

An example embodiment of the present invention has been described above. Those skilled in the art will understand, however, that changes and modifications can be made to this embodiment without departing from the true scope and spirit of the invention, which is defined by the claims.

What is claimed:

1. A computer-implemented method performed by a magnetic resonance imaging (MRI) system, the MRI system including one or more processors, memory, a main magnet, one or more gradient coils, and machine-readable instructions stored in the memory that, when executed by the one or more processors, cause the MM system to carry out functions performing the method, the method comprising:

while inducing a mechanical vibration in an object in the MM system, applying a magnetic resonance (MR) signal to the object, the MR signal having a phase;

encoding vibrational motion of the object in the MR signal phase simultaneously in three spatial dimensions by applying a motion encoding gradient (MEG) to the object simultaneously in the three spatial dimensions; and simultaneously acquiring in all three of the spatial dimensions magnetic resonance elastography (MRE) data including the MR signal phase encoded with the vibrational motion of the object in the three spatial dimensions, wherein encoding the vibrational motion of the object in the MR signal phase simultaneously in the three spatial dimensions by applying the MEG to the object simultaneously in the three spatial dimensions comprises:

in each respective dimension of the three spatial dimensions, simultaneously applying a respective spatial component of the MEG in a respective temporal sequence of N MEG application intervals, each MEG application interval including one or more MEG cycles of a periodic MEG applied in the respective dimension, and each given MEG application interval having a MEG start time measured with respect to a particular phase of the mechanical vibration, wherein the MEG start time of the given MEG application interval is determined based on both the respective spatial component and an ordinal position of the given MEG application interval in the respective temporal sequence of the respective spatial component; and over a time duration of each MEG application interval in each respective dimension, encoding in the MR signal phase a vibrational displacement in the respective dimension.

2. The method of claim 1, wherein the three spatial dimensions are three orthogonal spatial dimensions.

3. The method of claim 2, wherein the three orthogonal spatial dimensions correspond to three Cartesian directions x, y, and z, and further correspond to read, phase, and slice directions of the MM system.

4. The method of claim 1, further comprising generating a magnetic resonance elastogram from the simultaneously acquired MRE data.

5. The method of claim 4, wherein generating the magnetic resonance elastogram from the simultaneously acquired MRE data comprises generating MRE images in all three spatial dimensions that are aligned in space and in time.

6. The method of claim 4, further comprising calculating a mechanical property of the object from the simultaneously acquired MRE data.

7. The method of claim 6, wherein calculating the mechanical property of the object from the simultaneously acquired MRE data comprises separating shear from a compression wave by analysis of the simultaneously acquired MRE data.

8. The method of claim 1, wherein encoding the vibrational motion of the object in the MR signal phase simultaneously in the three spatial dimensions by applying the MEG to the object simultaneously in the three spatial dimensions comprises:

simultaneously encoding a displacement in each of the three spatial dimensions of an isochromat in the MR signal phase, the displacement in each of the three spatial dimensions corresponding to the induced mechanical vibration in the object in each of the three spatial dimensions.

9. The method of claim 1, wherein encoding the vibrational motion of the object in the MR signal phase simultaneously in the three spatial dimensions by applying the MEG to the object simultaneously in the three spatial dimensions comprises:

simultaneously encoding three respective spatial components of the vibrational motion of the object in the MR signal phase, each respective spatial component being encoded with a different sampling frequency.

10. The method of claim 9, wherein the MR signal phase encoded with the vibrational motion of the object is a harmonic function of a start time of a MEG application interval in each respective dimension of the three spatial dimensions, the start time of the MEG application interval in each respective dimension being a start time of one or more MEG cycles of a periodic MEG applied in the respective dimension, and being measured with respect to a particular phase of the mechanical vibration.

11. The method of claim 1, wherein N=8 for all three spatial dimensions.

12. The method of claim 1, wherein the time duration of each MEG application interval is the same, wherein the arithmetic difference between MEG start times of successive MEG application intervals for each respective spatial component corresponds to a respective sampling interval for the respective spatial component, wherein the arithmetic inverse of the respective sampling interval for the respective spatial component corresponds to a sampling frequency for the respective spatial component, and wherein encoding in the MR signal phase a vibrational displacement in the respective dimension comprises determining an encoded MR signal phase for each of N samples in each of the three spatial dimensions.

13. The method of claim 12, wherein the encoded MR signal phase of the nth of the N samples, n=0, 1, ..., N−1, is expressed analytically as:

$$\phi_n = \sum_{j=1}^{3} \varphi_j(s_{jn}) \xi_j u_j^0 \sin\left(2\pi j \frac{n}{N} + \Theta_j + \frac{\pi}{2}\right),$$

wherein the respective sampling interval in the jth spatial component, j=1, 2, 3, is given by $$\Delta t_j = \frac{j}{fN},$$

wherein $s_{jn}$=$n\Delta_j$, n=0, 1, ..., N−1 is the MEG start time, measured with respect to the particular phase of the mechanical vibration, for the nth sample in the jth spatial component, and wherein $u_j^0$ is a displacement amplitude in the jth spatial component due to vibrational motion, $\xi_j$ is an encoding efficiency in the jth spatial component, and $\Theta_j$ is an initial phase of the mechanical vibration in the jth spatial component at the initial time.

14. The method of claim 13, wherein simultaneously acquiring in all three of the spatial dimensions MRE data including the MR signal phase encoded with the vibrational motion of the object the three spatial dimensions comprises applying a discrete Fourier transform to $\phi_n$ to decompose individual components of displacement encoded in the MR signal phase.

15. The method of claim 1, wherein simultaneously acquiring in all three of the spatial dimensions MRE data including the MR signal phase encoded with the vibrational motion of the object the three spatial dimensions comprises storing encoded vibrational motion in the three spatial dimensions in a same k-space.

16. A magnetic resonance imaging (MRI) system comprising:

one or more processors;

memory;

a main magnet;

one or more gradient coils; and machine-readable instructions stored in the memory that, when executed by the one or more processors, cause the MM system to carry out functions including:

inducing a mechanical vibration in an object in the MRI system, while applying a magnetic resonance (MR) signal to the object, wherein the MR signal has a phase;

encoding vibrational motion of the object in the MR signal phase simultaneously in three spatial dimensions by applying a motion encoding gradient (MEG) to the object simultaneously in the three spatial dimensions; and simultaneously acquiring in all three of the spatial dimensions magnetic resonance elastography (MRE) data including the MR signal phase encoded with the vibrational motion of the object in the three spatial dimensions,
wherein encoding the vibrational motion of the object in the MR signal phase simultaneously in the three spatial dimensions by applying the MEG to the object simultaneously in the three spatial dimensions comprises:
in each respective dimension of the three spatial dimensions, simultaneously applying a respective spatial component of the MEG in a respective temporal sequence of N MEG application intervals, wherein each MEG application interval includes one or more MEG cycles of a periodic MEG applied in the respective dimension, and each given MEG application interval has a MEG start time measured with respect to a particular phase of the mechanical vibration, and wherein the MEG start time of the given MEG application interval is determined based on both the respective spatial component and an ordinal position of the given MEG application interval in the respective temporal sequence of the respective spatial component; and
over a time duration of each MEG application interval in each respective dimension, encoding in the MR signal phase a vibrational displacement in the respective dimension.

17. The MM system of claim 16, wherein the three spatial dimensions are three orthogonal spatial dimensions.

18. The MRI system of claim 17, wherein the three orthogonal spatial dimensions correspond to three Cartesian directions x, y, and z, and further correspond to read, phase, and slice directions of the MM system.

19. The MM system of claim 16, wherein the functions further comprise generating a magnetic resonance elastogram from the simultaneously acquired MRE data.

20. The MM system of claim 19, wherein generating the magnetic resonance elastogram from the simultaneously acquired MRE data comprises generating MRE images in all three spatial dimensions that are aligned in space and in time.

21. The MM system of claim 19, wherein the functions further comprise calculating a mechanical property of the object from the simultaneously acquired MRE data.

22. The MRI system of claim 21, wherein calculating the mechanical property of the object from the simultaneously acquired MRE data comprises separating shear from a compression wave by analysis of the simultaneously acquired MRE data.

23. The MM system of claim 16, wherein encoding the vibrational motion of the object in the MR signal phase simultaneously in the three spatial dimensions by applying the MEG to the object simultaneously in the three spatial dimensions comprises:
simultaneously encoding a displacement in each of the three spatial dimensions of an isochromat in the MR signal phase, wherein the displacement in each of the three spatial dimensions corresponds to the induced mechanical vibration in the object in each of the three spatial dimensions.

24. The MM system of claim 16, wherein encoding the vibrational motion of the object in the MR signal phase simultaneously in the three spatial dimensions by applying the MEG to the object simultaneously in the three spatial dimensions comprises:
simultaneously encoding three respective spatial components of the vibrational motion of the object in the MR signal phase, wherein each respective spatial component is acquired with a different sampling frequency by modulation of a sampling interval.

25. The MM system of claim 24, wherein the MR signal phase encoded with the vibrational motion of the object is a harmonic function of a start time of a MEG application interval in each respective dimension of the three spatial dimensions, wherein the start time of the MEG application interval in each respective dimension is a start time of one or more MEG cycles of a periodic MEG applied in the respective dimension, and is measured with respect to a particular phase of the mechanical vibration.

26. The MRI system of claim 16, wherein N=8 for all three spatial dimensions.

27. The MRI system of claim 16, wherein the time duration of each MEG application interval is the same,
wherein the arithmetic difference between MEG start times of successive MEG application intervals for each respective spatial component corresponds to a respective sampling interval for the respective spatial component,
wherein the arithmetic inverse of the respective sampling interval for the respective spatial component corresponds to a MEG modulation frequency for the respective spatial component,
and wherein encoding in the MR signal phase a vibrational displacement in the respective dimension comprises determining an encoded MR signal phase for each of N samples in each of the three spatial dimensions.

28. The MRI system of claim 27, wherein the encoded MR signal phase of the nth of the N samples, n=0, 1, ..., N−1, is expressed analytically as:

$$\phi_n = \sum_{j=1}^{3} \varphi_j(s_{jn}) = \sum_{j=1}^{3} \xi_j u_j^0 \sin\left(2\pi j \frac{n}{N} + \Theta_j + \frac{\pi}{2}\right),$$

wherein the respective sampling interval in the jth spatial component, j=1, 2, 3, is given by $$\Delta t_j = \frac{j}{fN},$$

wherein $s_{jn} = n\Delta t_j$, n=0, 1, ..., N−1 is the MEG start time, measured with respect to the particular phase of the mechanical vibration, for the nth sample in the jth spatial component,
and wherein $u_j^0$ is a displacement amplitude in the jth spatial component due to vibrational motion, $\xi_j$ is an encoding efficiency in the jth spatial component, and $\Theta_j$ is an initial phase of the mechanical vibration in the jth spatial component at the initial time.

29. The MRI system of claim 28, wherein simultaneously acquiring in all three of the spatial dimensions MRE data including the MR signal phase encoded with the vibrational motion of the object the three spatial dimensions comprises applying a discrete Fourier transform to $\phi_n$ to decompose individual components of displacement encoded in the MR signal phase.

30. The MRI system of claim 16, wherein simultaneously acquiring in all three of the spatial dimensions MRE data including the MR signal phase encoded with the vibrational motion of the object the three spatial dimensions comprises storing encoded vibrational motion in the three spatial dimensions in a same k-space.

\* \* \* \* \*

UNITED STATES PATENT AND TRADEMARK OFFICE
CERTIFICATE OF CORRECTION

PATENT NO.         : 9,995,813 B2
APPLICATION NO.    : 14/648081
DATED              : June 12, 2018
INVENTOR(S)        : Dieter Klatt and Temel Kaya Yasar It is certified that error appears in the above-identified patent and that said Letters Patent is hereby corrected as shown below:

In the Claims

In Column 18, Line 37: please delete "MM" and insert -- MRI --.

In Column 18, Line 40: please delete "MM" and insert -- MRI --.

In Column 19, Line 12: please delete "MM" and insert -- MRI --.

In Column 20, Line 57: please delete "MM" and insert -- MRI --.

In Column 21, Line 27: please delete "MM" and insert -- MRI --.

In Column 21, Line 32: please delete "MM" and insert -- MRI --.

In Column 21, Line 33: please delete "MM" and insert -- MRI --.

In Column 21, Line 36: please delete "MM" and insert -- MRI --.

In Column 21, Line 41: please delete "MM" and insert -- MRI --.

In Column 21, Line 49: please delete "MM" and insert -- MRI --.

In Column 21, Line 60: please delete "MM" and insert -- MRI --.

In Column 22, Line 3: please delete "MM" and insert -- MRI --.

Signed and Sealed this
Fourteenth Day of August, 2018

Andrei Iancu
*Director of the United States Patent and Trademark Office*